United States Patent [19]

Chou et al.

[11] Patent Number: 5,256,797
[45] Date of Patent: Oct. 26, 1993

[54] PROCESS FOR SEPARATING 2-DEOXY-2,2-DIFLUORO-D-RIBOFURANOSYL ALKYLSULFONATE ANOMERS

[75] Inventors: Ta-Sen Chou, Indianapolis; Timothy J. McCarthy, Flora, both of Ind.

[73] Assignee: Eli Lilly and Company, Indianapolis, Ind.

[21] Appl. No.: 902,303

[22] Filed: Jun. 22, 1992

[51] Int. Cl.$^5$ ............................................. C07D 307/20
[52] U.S. Cl. .................................... 549/478; 549/476
[58] Field of Search .................. 549/475, 476, 478

[56] References Cited

U.S. PATENT DOCUMENTS

| | | | |
|---|---|---|---|
| 4,526,988 | 7/1985 | Hertel | 549/313 |
| 4,965,374 | 10/1990 | Chou et al. | 549/313 |

Primary Examiner—C. Warren Ivy
Assistant Examiner—A. A. Owens
Attorney, Agent, or Firm—Sidney Persley; Leroy Whitaker

[57] ABSTRACT

A process for separating an anomeric mixture of alpha and beta 2-deoxy-2,2-difluoro-D-ribofuranosyl-1-alkylsulfonates by contacting the anomeric mixture with a solvent; heating; adding a countersolvent; and lowering the temperature.

11 Claims, No Drawings

PROCESS FOR SEPARATING 2-DEOXY-2,2-DIFLUORO-D-RIBOFURANOSYL ALKYLSULFONATE ANOMERS

BACKGROUND OF THE INVENTION

1. Field of the Invention

The invention pertains to a process for separating and crystallyzing anomers of of 2-deoxy-2,2-difluoro-D-ribofuranosyl-1-alkylsulfonate from an anomeric mixture.

2. State of the Art

M. Hofer, Chem. Ber., 93, 277 (1960) and Bhahacharya, J Org. Chem., 28, 428 (1963) described a process for preparing 1-chloro-2-deoxy-3,5-O-(di-p-toluoyl)-D-erythro-pentofuranose. Since the α-anomer was crystalline, it could be separated by filtration from the β-anomer and obtained in the pure crystalline form. Thus, the crystalline chloride has become the predominant substrate for the synthesis of β-nucleosides from 2-deoxyribofuranosyl derivatives.

The 2-deoxyribofuranosyl alkylsulfonate derivatives are unstable compounds. Therefore, there is little mention of them in the chemical literature. However, 2-deoxy-2,2-difluoro-D-ribofuranosyl-1-alkylsulfonate derivatives are stable compounds because of the presence of a gem-difluoro moiety at the 2-position. For instance, 2-deoxy-2,2-difluoro-D-ribofuranosyl-1-methanesulfonate are used in U.S. Pat. Nos. 4,526,988 and 4,965,374 in the preparation of pyrimidine and purine nucleosides. However, the 2-deoxy-2,2-difluoro-D-ribofuranosyl-1-methanesulfonates were anomeric mixtures and no attempt was made to separate the pure anomers. As a result the nucleoside syntheses were non-stereoselective.

To prepare 2'-deoxy-2',2'-difluororibofuranosyl nucleosides stereoselectively requires a high purity alpha or beta anomer of 2-deoxy-2,2-difluoro-D-ribofuranosyl alkylsulfonate derivatives. Since, these alkyl sulfonate derivatives are usually produced as an anomeric mixture there is a need for a process for separating the respective anomers.

An objective of the present invention is to provide a process for separating an anomeric mixture of alpha and beta 2-deoxy-2,2-difluoro-D-ribofuranosyl alkylsulfonates.

Another objective of the present invention is to provide a process for separating an anomeric mixture of alpha and beta 2-deoxy-2,2-difluoro-D-ribofuranosyl alkylsulfonates that produce the anomers in crystalline form.

Other objects and advantages of the present invention will become apparent from the following description of embodiments.

SUMMARY OF THE INVENTION

The invention is a process for separating an anomeric mixture of alpha and beta anomers of the formula

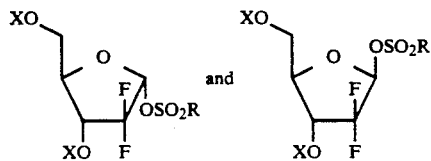

wherein each X is independently selected from hydroxy protecting groups and R is an alkyl or substituted alkyl; comprising contacting the anomeric mixture with a solvent; heating; adding a countersolvent; and lowering the temperature.

DETAILED DESCRIPTION OF THE INVENTION

Throughout this document, all temperatures are in degrees Celsius, all proportions, percentages and the like, are in weight units and all mixtures are in volume units, except where otherwise indicated. Anomeric mixtures are expressed as a percent. The term "xylenes" alone or in combination refers to all isomers of xylene and mixtures thereof. The term "sulfonate" alone or in combination refers to compounds of the general formula $RSO_3$; wherein R is alkyl or substituted alkyl. The term "alkyl" alone or in combination refers to straight and branched chain aliphatic hydrocarbon groups which preferably contain up to 7 carbon atoms, such as methyl, ethyl, n-propyl, isopropyl, n-butyl, t-butyl, n-pentyl, n-hexyl, 3-methylpentyl groups and the like, or substituted straight and branched chain aliphatic hydrocarbons such as chloroethane, 1,2-dichloroethane, and the like. The term "substituted" alone or in combination refers to the replacement of hydrogen or a common moiety by one or more of the groups selected from cyano, halo, carboalkoxy, toluoyl, nitro, alkoxy, alkyl, and dialkylamino.

The anomeric mixture of 3,5-hydroxy protected 2-deoxy-2,2-difluoro-D-ribofuranosyl-1-alkylsulfonate starting material suitable for use in the present separation process are described in U.S. Pat. No. 4,526,988, U.S. Pat. No. 4,965,374, Pending U.S. patent application Ser. No. 07/902,305, filed contemporaneosly herewith and Pending U.S. patent application Ser. No. 07/902,301, Attorney Docket X8623, filed contemporaneously herewith. In a preferred embodiment of the present process an anomeric mixture of 2-deoxy-2,2-difluoro-D-ribofuranosyl-3,5-di-0-benzoyl-1-methanesulfonate, 2-deoxy-2,2 difluoro-D-ribofuranosyl-3,5-di-O-benzoyl-1-ethanesulfonate or substituted forms thereof are used as starting materials.

The hydroxy protecting groups (X) are known in the art and are described in Chapter 3 of *Protective Groups in Organic Chemistry*, McOmie Ed., Plenum Press, New York (1973), and Chapter 2 of *Protective Groups in Organic Synthesis*, Green, John, J. Wiley and Sons, New York (1981); preferred are ester forming groups such as formyl, acetyl, substituted acetyl, propionyl, butynyl, pivaloyl, 2-chloroacetyl, benzoyl, substituted benzoyl, phenoxycarbonyl, methoxyacetyl; carbonate derivatives such as phenoxycarbonyl, t-butoxycarbonyl ethoxycarbonyl, vinyloxycarbonyl, 2,2,2-trichloroethoxycarbonyl and benzyloxycarbonyl; alkyl ether forming groups such as benzyl, diphenylmethyl, triphenylmethyl, t-butyl, methoxymethyl, tetrahydropyranyl, allyl, tetrahydrothienyl, 2-methoxyethoxy methyl; and silyl ether forming groups such as trialkylsilyl, trimethylsilyl, isopropyldialkylsilyl, alkyldiisopropylsilyl, triisopropylsilyl, t-butyldialkylsilyl and 1,1,3,3,-tetraisopropyldisloxanyl; carbamates such as N-phenylcarbamate and N-imidazoylcarbamate; however more preferred are benzoyl, mono-substituted benzoyl and disubstituted benzoyl, acetyl, pivaloyl, triphenylmethyl ethers, and silyl ether forming groups, especially t-butyldimethylsilyl; while most preferred is benzoyl.

Solvents suitable for use in the present process may be selected from the group consisting of dichloromethane, 1,2-dichloroethane, 1,1,2-trichloroethane, propyl acetate, isopropyl acetate, amyl acetate, anisole, toluene, xylenes, and mixtures thereof; preferred are propyl acetate, 1,2-dichloroethane, anisole, and mixtures thereof.

After the solvent is added to an anomeric mixture of 3,5-hydroxy protected 2-deoxy-2,2-difluoro-D-ribofuranosyl-1-alkylsulfonate, the solution is heated from about 30° C. to about 50° C. to form a solution.

The counter solvent is then added to the solution. Suitable counter solvents for use in the present process may be selected from the group consisting of ethanol, denatured ethanol (denatured with methanol, toluene, ethyl acetate, isopropyl alcohol, methyl isobutyl ketone, or mixtures thereof), isopropyl alcohol, methanol, ethanol, methyl-t-butyl ether, diethyl ether, and mixtures thereof; preferred are ethanol and isopropyl alcohol.

The temperature of the mixture is then lowered in to about 23° C. to about −10° C. and more preferably to about 23° C. to about 5° C.

In a preferred embodiment 3,5-hydroxy protected 2-deoxy-2,2-difluoro-D-ribofuranosyl-1-α-alkylsulfonate crystals such as 2-deoxy-2,2-difluoro-D-ribofuranosyl 3,5-di-O-benzoyl-1-α-methanesulfonate crystals are formed when the temperature is lowered.

The present process is a true crystallization and not a precipitation of an amorphous solid material. The crystals formed contain a well developed crystal face and have a high birefringence when viewed by crystallagraphic microscopy.

When the anomeric ratio is below 50 percent alpha anomer in the present process, in the absence of a spontaneous crystallization of anomers, it may be necessary to add some seed crystals of the alpha anomer to achieve crystallization.

The present process is preferably carried out under atmospheric conditions and is substantially complete in about 30 minutes to about 20 hours, and more preferably complete in about 2 hours.

The present process is particularly advantageous because of its simplicity and the unexpected yields which correspond to the obtention of an individual anomer in quantities greater than present in the anomeric mixture. When applied to an alpha and beta-anomer mixture of 2-deoxy-2,2-difluoro-D-ribofuranosyl-3,5-di-0-benzoyl-1-alkylsulfonate, the present process permits obtention of the alpha anomer in crystalline form which is of particular interest since it is useful in the glycoslation of biologically important beta-anomer nucleosides.

The following examples illustrate specific aspects of the present invention and are not intended to limit the scope thereof in any respect and should not be so construed.

EXAMPLE 1

A anomeric mixture of 2-deoxy-2,2-difluoro-D-ribofuranosyl-3,5-di-O-benzoyl-1-methanesulfonate (11.9 g) in dichloromethane (45 ml) was heated to 30° C. Diethyl ether was added until the solution became cloudy (about 45 ml) As the solution was slowly cooled to room temperature, dense, cubic-like crystals formed. After 2 hours at room temperature, a needle-like crystal began to form, at which time the supernatant was decanted. The cube-like crystals were collected, rinsed with a 3:1 solution of dichloromethane and diethyl ether and then dried. Physical data analysis showed that the cube-crystals to be 2-deoxy-2,2-difluoro-D-ribofuranosyl-3,5-di-O-benzoyl-1-β-methanesulfonate. A few hours later, the needle-like crystals in the mother liquor were collected by filtration. A physical data analysis of the needle-like crystals showed them to be 2-deoxy-2,2-difluoro-D-ribofuranoysl-3,5-di-O-benzoyl-1-α-methanesulfonate. m.p. 88° C.-89° C.; $[\alpha]_D(C=1.01$, solvent: $CHCl_3$ @589 nm) +84.2°; $[\alpha]_{365}(C=1.01$, solvent: $CHCl_3$, @365 nm) +302.0°, FDMS 456 (m+1).

EXAMPLE 2

An anomeric mixture of 2-deoxy-2,2-difluoro D-ribofuranosyl-3,5-di-O-benzoyl-1-methanesulfonate (11.53 g, 78% alpha and 22% beta anomer) in anisole (35 ml) was heated to 30° C.-40° C. 3A-alcohol (145 ml) was added and the solution was cooled to 15° C. After seeding the solution with 2-deoxy-2,2-difluoro-D-ribofuranosyl-3,5-di-O-benzoyl-1-α-methanesulfonate crystals (0.1 g–0.3 g), the slurry was kept at 5° C. for 18 hours. The 2-deoxy-2,2-difluoro-D-ribofuranosyl-3,5-di-O-benzoyl-1-α-methanesulfonate crystals harvested weighed 5.7 g. The yield was 49.8 percent. The filtrate contained a 1:1 ratio of the two anomers.

EXAMPLE 3

An anomeric mixture of 2-deoxy-2,2-difluoro-D-ribofuranosyl-3,5-di-O-benzoyl-1-methanesulfonate (11.9 g, 78% alpha and 22% beta anomer) in anisole (24 ml) was heated to 30° C.-40° C. 3A alcohol (120 ml) was added and the solution was cooled to 30° C. After seeding the solution with 2-deoxy-2,2-difluoro-D-ribofuranosyl-3,5-di-O-benzoyl-1-α-methanesulfonate crystals (0.1 g - 0.3 g), the slurry was kept at 5° C. for 17 hours. The 2-deoxy-2,2-difluoro-D-ribofuranosyl-3,5-di-O-benzoyl-1-α-methanesulfonate crystals harvested weighed 6.2 g. The yield was 55 percent.

EXAMPLE 4

An anomeric mixture of 2-deoxy-2,2-difluoro-D-ribofuranosyl-3,5-di-O-benzoyl-1-methanesulfonate (11.9 g, 78% alpha and 22% beta anomer) in dichloromethane (12 ml) was heated to 40° C. 3A alcohol (24 ml) was added and the temperature of the solution was reduced to 30° C. After seeding the solution with 2-deoxy-2,2-difluoro-D-ribofuranosyl-3,5-di-O-benzoyl-1-α-methanesulfonate crystals (0.1 g–0.3 g), the slurry was kept at 5° C. for 17 hours. The 2-deoxy-2-difluoro-D-ribofuranosyl-3,5-di-O-benzoyl-1-α-methanesulfonate crystals harvested weighed 5.9 g. The yield was 51 percent.

EXAMPLE 5

An anomeric mixture of 2-deoxy-2,2-difluoro-D-ribofuranosyl-3,5-di-O-benzoyl-1-methanesulfonate (11.9 g, 78% alpha and 22% beta anomer) in 1,2-dichloroethane (12 ml) was heated to 30° C.-40° C. 3A alcohol (36 ml) was added and the solution was cooled to 23° C. After seeding the solution with 2-deoxy-2,2-difluoro-D-ribofuranosyl-3,5-di-O-benzoyl-1-α-methanesulfonate crystals (0.1 g - 0.3 g), the slurry was kept at 5° C. for 17 hours. The 2-deoxy-2-difluoro-D-ribofuranosyl-3,5-di-O-benzoyl-1-α-methanesulfonate crystals harvested weighed 7.3 g. The yield was 61 percent.

EXAMPLE 6

An anomeric mixture of 2-deoxy-2,2-difluoro-D-ribofuranosyl-3,5-di-O-benzoyl-1-methanesulfonate (25 g, 70% alpha and 30 beta anomer) was heated to 30°

C.–40° C. in ethanol (300 ml). Next, anisole (72 ml) was added and the temperature of the solution was reduced to 15° C. After seeding the solution with 2-deoxy-2,2-difluoro-D-ribofuranosyl-3,5-di-O-benzoyl-1-α-methanesulfonate crystals (0.1 g - 0.3 g), the slurry was kept at 5° C. for 3 hours. The 2-deoxy-2,2-difluoro-D-ribofuranosyl-3,5-di-O-benzoyl-1-α-methanesulfonate crystals harvested weighed 13.5 g. The yield was 52 percent.

EXAMPLE 7

An anomeric mixture of 2-deoxy-2,difluoro-D-ribofuranosyl-3,5-di-O-benzoyl-1-methanesulfonate (3.38 g, 70% alpha and 30% beta anomer) was heated to 30° C.–40° C. in amyl acetate (8.3 ml). Next, ethanol (40 ml) was added and the temperature of the solution was reduced to 15° C. After seeding the solution with 2-deoxy-2,2-difluoro-D-ribofuranosyl-3,5-di-O-benzoyl-1-α-methanesulfonate crystals (0.1 g - 0.3 g), the slurry was kept at 5° C. for 3 hours. The 2-deoxy-2,2-difluoro-D-ribofuranosyl-3,5-di-O-benzoyl-1-α-methanesulfonate crystals harvested weighed 2.31 g. The yield was 68 percent.

EXAMPLE 8

An anomeric mixture of 2-deoxy,2-difluoro-D-ribofuranosyl-3,5-di-O-benzoyl-1-methanesulfonate (12 g, 80% alpha and 20% beta anomer) was heated to 30° C.–40° C. in dichloromethane. The dichloromethane was then removed via vacuum distillation. Next, a mixture of anisole (48 ml) and ethanol (144 ml) was added and the temperature of the solution was reduced to 0° C. to 5° C. After 2 hours, the 2-deoxy-2,2-difluoro-D-ribofuranosyl -3,5-di-O-benzoyl-1-α-methanesulfonate crystals harvested weighed 4.6 g. The yield was 38 percent.

EXAMPLE 9

An anomeric mixture of 2-deoxy,2-difluoro-D-ribofuranosyl 3,5-di-O-benzoyl-1-methanesulfonate (7.3 g, 68% alpha and 31% beta anomer) was heated to 30° C.–40° C. in dichloromethane. The dichloromethane was then removed via vacuum distillation. Next, a mixture of propyl acetate (20 ml) and ethanol (70 ml) was added and the temperature of the solution was reduced to 15° C. After seeding the solution with 2-deoxy-2,2-difluoro-D-ribofuranosyl-3,5-di-O-benzoyl-1-α-methanesulfonate crystals (0.1 g–0.3 g), the slurry was kept at 15° C. for 3 hours. The 2-deoxy-2,2-difluoro-D-ribofuranosyl-3,5-di-O-benzoyl -1-α-methanesulfonate crystals harvested weighed 4.62 g. The yield was 63 percent.

EXAMPLE 10

An anomeric mixture of 2-deoxy,2-difluoro-D-ribofuranosyl-3,5-di-O-benzoyl-1-methanesulfonate (100 g, 66% alpha and 33% beta anomer) was heated to 50° C. in isoamyl acetate (290 ml). Next, ethanol (1200 ml) was added and the temperature of the solution was reduced to 15° C. After seeding the solution with 2-deoxy-2,2-difluoro-D-ribofuranosyl-3,5-di-O-benzoyl-1-α-methanesulfonate crystals (0.1 g–0.3 g), the slurry was kept at 5° C. for 3 hours. The 2-deoxy-2,2-difluoro-D-ribofuranosyl-3,5-di-O-benzoyl-1-α-methanesulfonate crystals harvested weighed 36.7 g. The yield was 35.5 percent.

The present invention has been described in detail including the perfected embodiments thereof. However, it will be appreciated that those skilled in the art, upon consideration of the present disclosure, may make modifications and/or improvements on this invention that fall within the scope and spirit of the inventions as set forth in the following claims.

What is claimed is:

1. A process for separating an anomeric mixture of alpha and beta anomers of the formula:

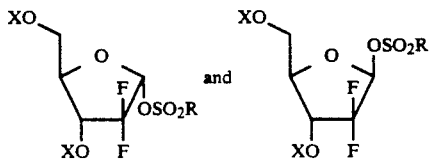

wherein each X is independently selected from hydroxy protecting groups and R is an alkyl or substituted alkyl; comprising contacting the anomeric mixture with a solvent; heating; adding a countersolvent; and lowering the temperature.

2. The process of claim 1 wherein the solvent is selected from the group consisting of dichloromethane, 1,2-dichloroethane, 1,1,2-trichloroethane, propyl acetate, isopropyl acetate, amyl acetate, anisole, toluene, xylenes, and mixtures thereof.

3. The process of claim 2 wherein the solvent is selected from 1,2-dichloroethane, propylacetate, and mixtures thereof.

4. The process of claim 1 wherein the heating is from about 30° C. to about 50° C.

5. The process of claim 1 wherein the countersolvent is selected from the group consisting of ethanol, denatured ethanol, isopropyl alcohol, methanol, methyl-t-butyl ether, diethyl ether, and mixtures thereof.

6. The process of claim 5 wherein the countersolvent is selected from the group consisting of isopropyl alcohol, ethanol, and mixtures thereof.

7. The process of claim 1 wherein the temperature is lowered to about 23° C. to about −10° C.

8. The process of claim 7 wherein the temperature is lowered to about 23° C. to about 5° C.

9. The process of claim 1 wherein R is selected from mehtyl, ethyl, and substituted forms thereof.

10. The process of claim 1 wherein R is methyl.

11. The process of claim 1 wherein 2-deoxy-2,2-difluoro-D-ribofuranosyl-3,5-di-O-benzoyl-1-α -methanesulfonate forms as crystals upon lowering the temperature.

* * * * *

UNITED STATES PATENT AND TRADEMARK OFFICE
CERTIFICATE OF CORRECTION

PATENT NO.   :   5,256,797

DATED        :   October 26, 1993

INVENTOR(S)  :   Ta-Sen Chou, et al.

It is certified that an error appears in the above-identified patent and that said Letters Patent is hereby corrected as shown below:

Column 5, lines 15-16, "(3.38 g,        70% alpha and 30% beta anomer)" should read --(3.38 g, 70% alpha and 30% beta anomer)--.

Column 6, line 54, "mehtyl" should read --methyl--.

Column 6, line 57, "benzoyl-1-60" should read --benzoyl-1-α--.

Signed and Sealed this

Sixth Day of December, 1994

Attest:

BRUCE LEHMAN

Attesting Officer

Commissioner of Patents and Trademarks